*(12)* United States Patent
Casanova et al.

US010085948B2

(10) Patent No.: US 10,085,948 B2
(45) Date of Patent: Oct. 2, 2018

(54) IONIC GELATION ON SOLIDS

(71) Applicant: UNIVERSIDAD DE ANTIOQUIA (UDEA), Medellín (CO)

(72) Inventors: Herley Fernando Casanova, Medellín (CO); César Perez Zapata, Medellín (CO); César Restrepo, Medellín (CO); Johnatan Diosa Arango, Medellín (CO)

(73) Assignee: Universidad de Antioquia (UDEA), Medellin (CO)

( * ) Notice: Subject to any disclaimer, the term of this patent is extended or adjusted under 35 U.S.C. 154(b) by 0 days.

(21) Appl. No.: 14/914,836

(22) PCT Filed: Aug. 21, 2014

(86) PCT No.: PCT/IB2014/064016
§ 371 (c)(1),
(2) Date: Feb. 26, 2016

(87) PCT Pub. No.: WO2015/028920
PCT Pub. Date: Mar. 5, 2015

(65) Prior Publication Data
US 2016/0271071 A1 Sep. 22, 2016

(30) Foreign Application Priority Data
Aug. 27, 2013 (CO) .................................. 13203104

(51) Int. Cl.
| | |
|---|---|
| *A61K 9/50* | (2006.01) |
| *C08K 9/10* | (2006.01) |
| *C08L 89/00* | (2006.01) |
| *C08L 5/00* | (2006.01) |
| *A61K 9/20* | (2006.01) |
| *A61K 9/48* | (2006.01) |
| *A61Q 19/00* | (2006.01) |
| *A61K 8/11* | (2006.01) |
| *A61K 8/64* | (2006.01) |
| *A61K 8/19* | (2006.01) |

(52) U.S. Cl.
CPC ............ *A61K 9/5089* (2013.01); *A61K 8/11* (2013.01); *A61K 8/19* (2013.01); *A61K 8/64* (2013.01); *A61K 9/2095* (2013.01); *A61K 9/485* (2013.01); *A61K 9/5052* (2013.01); *A61K 9/5073* (2013.01); *A61Q 19/00* (2013.01); *C08K 9/10* (2013.01); *C08L 5/00* (2013.01); *C08L 89/00* (2013.01); *A61K 2800/10* (2013.01)

(58) Field of Classification Search
CPC .... A61K 9/5052; A61K 9/5089; A61K 9/485; A61K 9/2095; A61K 9/5073; A61K 8/64; A61K 8/19; A61K 8/11; A61K 2800/10; C08L 89/00; C08L 5/00; C08K 9/10
See application file for complete search history.

(56) References Cited

U.S. PATENT DOCUMENTS

| | | | |
|---|---|---|---|
| 2007/0275080 A1 | 11/2007 | Laulicht et al. | |
| 2011/0107524 A1* | 5/2011 | Chieffi | A01N 25/28 8/137 |
| 2012/0156288 A1* | 6/2012 | Lakkis | A23P 10/30 424/455 |
| 2012/0216990 A1* | 8/2012 | Quintero | C09K 8/035 165/104.13 |
| 2012/0258150 A1* | 10/2012 | Rauckhorst | C11D 3/505 424/401 |

FOREIGN PATENT DOCUMENTS

| | | |
|---|---|---|
| EP | 0504387 A1 | 9/1992 |
| EP | 2359929 A1 | 8/2011 |
| WO | 1992005708 A1 | 4/1992 |

OTHER PUBLICATIONS

Eng. Translation of Patent DE 102008057186 A1, May 20, 2010, Ulrike et al.*
Kagami et al., "Oxidative Stability, Structure, and Physical Characteristics of Microcapsules Formed by Spray Drying of Fish Oil with Protein and Dextrin Wall Materials" in Journal of Food Science, vol. 68, No. 7, 2003, Food Engineering and Physical Properties.*
Anil, A et al, Ionotropic cross-linked chitosan microspheres for controlled release of ampicillin, Int'l J. of Pharm. 312:166-173 (2006).
Annan, N.T., et al., Encapsulation in alginate-coated gelatin microspheres improves survival of the probiotic Bifidobacterium adolescentis 15703T during exposure to simulated gastro-intestinal conditions, Food Res. Int'l, 41:184-193 (2008).
Arup Nag, et al., Microencapsulation of probiotic bacteria using pH-induced gelation of sodium caseinate and gellan gum, Int'l diary 1 21:247-253 (2011).
Casanova, H and Higuita, L, Synthesis of calcium carbonate nanoparticles by reactive precipitation using a high pressure jet homogenizer, Chem. Eng. J. 175:569-578 (2011).
Certificate of Correction—Priority Application.
(Continued)

*Primary Examiner* — Blessing M Fubara
(74) *Attorney, Agent, or Firm* — The Morales Law Firm, LLC; Joseph L. Morales (57) ABSTRACT

The invention relates to a method for ionic gelation on solids for encapsulating water-insoluble solids. The method uses negatively charged macromolecules and soluble salts of polyvalent cations as shell-forming materials having a high adsorption on the surface of the solid when subjected to thermal treatment. The shell-forming material represents at least 10% of the weight of the dry microcapsule obtained. The obtained microcapsule can be redispersed in water and treated by altering the environment thereof in order to be used as an encapsulating medium for water-soluble compounds and they can also be used as active ingredients and/or excipients in the production of pharmaceutical or nutraceutical compositions.

34 Claims, 6 Drawing Sheets

(56) References Cited

OTHER PUBLICATIONS

Dong, Q et al, Alginate-based and protein-based materials for probiotics encapsulation: a review; Int'l J. of Food Science and Tech. (2013).
Examination Report Colombian Priority Application (2015).
Issue Notification Priority Application.
Miladi, K., et al., Drug Carriers in osteoporosis: Preparation, drug encapsulation and applications, Int'l J. of Pharm. 445:181-195 (2013).
Munin, Aude and Edwards-Levy, Florence, Encapsulation of Natural Polyphenolic Compouns, a Review, Pharmaceutics 3:793-829 (2011).
P. Burey, et al., Hydrocolloid Gel Particles: Formation, Characterization, and Application, Critical Reviews in Food Science and Nutrition, 48(5):361-377 (2008).
Perez, C.A. et al., Brownian dynamics simulation of monolayer formation by deposition of colloidal particles: A kinetic study at high bulk particle concentration, Eur. Phys. J. E 35:69 (1-8) (2012).
Song, Huiyi et al., Microencapsulated probiotics using emulsification technique coupled with internal or external gelation process, Carbohydrate Polymers 96:181-189 (2013).
Souza, F. et al, Production and characterization of microparticles containing pectin and whey proteins, Food Res. Int'l 49:560-566 (2012).

\* cited by examiner

IONIC GELATION ON SOLIDS

TECHNICAL FIELD

The invention relates to a process for encapsulating water-insoluble solids that includes the addition of a negatively charged macromolecule to an aqueous suspension of the insoluble solid, followed by a thermal treatment and the addition of divalent ions to form a shell that covers the solid. The thermal treatment of the macromolecule and the addition of calcium salts, at the appropriate times and concentrations, induce the high adsorption (>80%) of these compounds to the surface of the insoluble solid particles, without causing colloidal destabilization (aggregate or lump formation), thereby producing a stable suspension of microcapsules.

By varying the drying conditions and the surface chemistry of the suspended microcapsules, it is possible to change the degree of aggregate formation of the dry microcapsules. This makes it possible to generate microcapsules of individual molecules or particle agglomerates.

BACKGROUND

The encapsulation of water-insoluble solids can be achieved by physical, physico-chemical, or chemical processes. Physical processes, such as spray-drying, fluidized bed coating or supercritical fluid spray coating all subject the material to be dried at above room temperature conditions, which can degrade thermolabile compounds (1). Therefore, physico-chemical processes, such as coacervation, or chemical processes, such as interfacial polymerization or enzymatic cross-linking, are microencapsulation alternatives that maintain the chemical integrity of the compounds to be encapsulated (2). The physico-chemical microencapsulation processes used to encapsulate insoluble solids usually employ methods based on ionic interactions, such as ionic gelation, acid precipitation, coacervation and layer-by-layer processes (2). These processes employ charged macromolecules, such as proteins, polysaccharides or synthetic polyelectrolites that interact electrostatically with other macromolecules or oppositely charged ions in the solution or on the surface of the solid to be encapsulated. Thus, a polymeric complex matrix gel that coats the solid of interest is generated. Microencapsulation by means of ionic gelation has advantages over the other methods based in ionic interactions, because it only uses one charged macromolecule, thereby simplifying the system and the costs of the process, as well as allowing greater control over the viscosity of the work system. Ionic gelation consists of the extrusion or emulsification of a charged macromolecule (e.g. sodium alginate) incorporated into drops, in a counter ion (e.g. calcium chloride) solution, leading to the immediate gelation of the exterior of the drop upon contact.

After that, the counter ions continue their diffusion toward the particle's interior and cause its complete gelation. However, the diffusion mechanism of the counter ion usually causes a heterogeneous gelation of the particle, which is not convenient for applications wherein the release kinetics of an active compound must be controlled (3). Ionic gelation through an internal gelation mechanism solves the drawback of diffusion gelation by employing an inactive form of the counter ion that is activated (e.g. by a change in pH) only after it is mixed with the macromolecule (3).

This ionic gelation method has been applied to the encapsulation of polyphenols (2), osteoporosis medications (4), probiotics (5, 6), antibiotics (7) and for generating biocompatible capsules of active compounds (8). However, one of the main inconveniences is the high porosity of the matrix-forming gel of the microcapsule, which allows a quick diffusion of the encapsulated compounds (9-11). This issue can be solved by generating a gel matrix based on proteins or a mix of proteins and polysaccharides through heating, enzymatic cross-linking, or acidification (1). Obtaining a gel matrix of the microparticle by heating (12) or acidification may not be viable for compounds that are sensitive to those environmental conditions, and in the case of cross-linking, its usage possibilities and cross-linking effectiveness are determined by the type of protein used, thereby limiting its range of applications. The prior art of the microencapsulation process by ionic gelation shows the need to generate a low-porosity gel matrix for the microparticle, based on proteins or a mix of proteins and polysaccharides, under conditions that do not include excessive heating nor acidification of the medium in its production.

The present invention, through a microencapsulation process, is able to achieve the formation of a matrix of charged macromolecules on the surface of water-insoluble solids, generating microspheres by controlled adsorption of the macromolecules to the surface of the solid in the presence of polyvalent ions at low temperature and its gelation by increasing the temperature to room temperature or higher, depending on the type of macromolecule being used.

BRIEF DESCRIPTION OF THE INVENTION

The present invention develops a process for the microencapsulation of water-insoluble solids through ionic gelation of macromolecules in the surface of the suspended solid particles with diameters between 0.1 and 1,000 micrometers. The suspended microcapsules can be dried using processes, such as spray-drying, to generate microspherical dry or agglomerated microcapsules that contain at least 10% by weight of shell-forming material relative to the weight of the dry microcapsule.

DETAILED DESCRIPTION OF THE INVENTION

Figure 1:
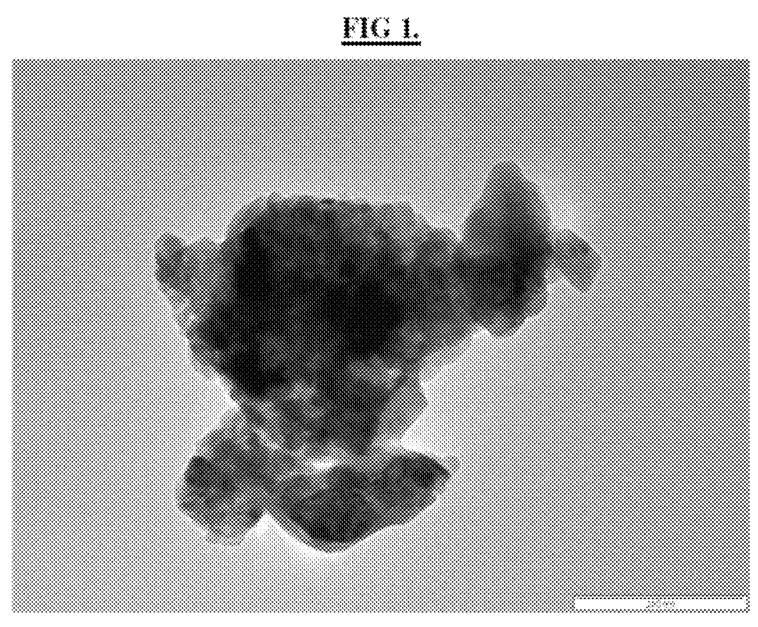
FIG. 1. Scanning electron micrograph of a calcium carbonate microcapsule, using sodium caseinate as the shell-forming compound (Example 1).
Figure 2:
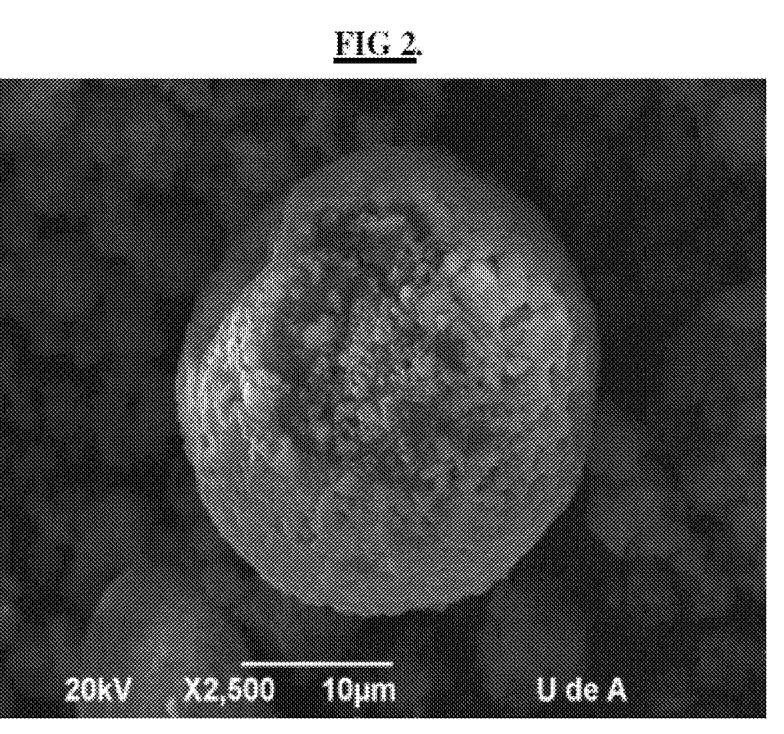
FIG. 2. Scanning electron micrograph of a calcium carbonate microcapsule, using sodium caseinate as the shell-forming compound (Example 1).
Figure 3:
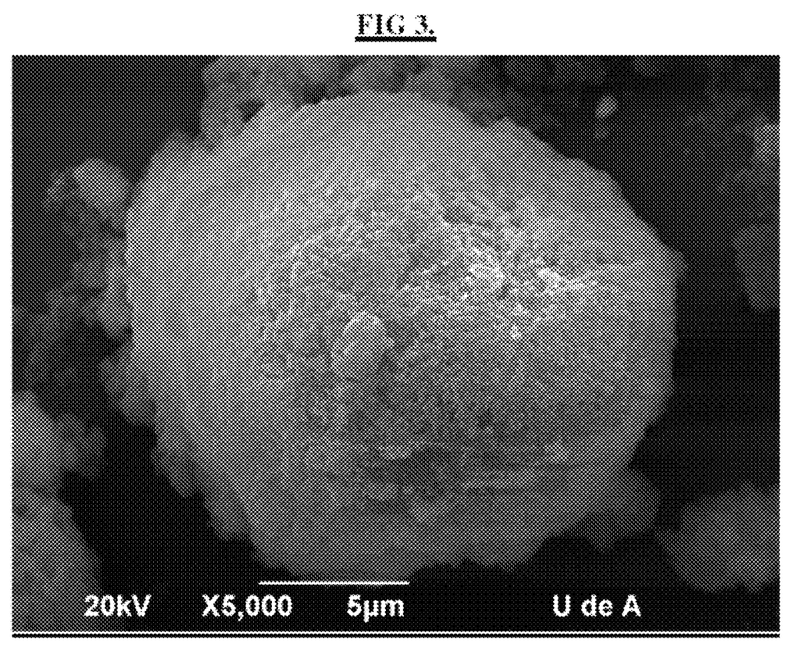
FIG. 3. Scanning electron micrograph of an acid-treated calcium carbonate/calcium phosphate microcapsule, using sodium caseinate as the shell-forming compound (Example 2).
Figure 4:
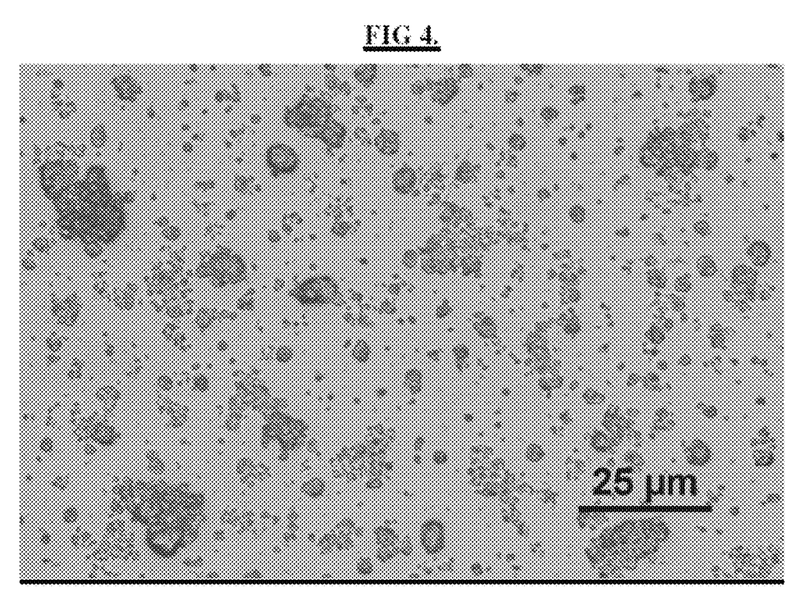
FIG. 4. Optic photomicrograph of acid-treated calcium carbonate/calcium phosphate microcapsules with encapsulated cresyl violet (Example 2).
Figure 5:
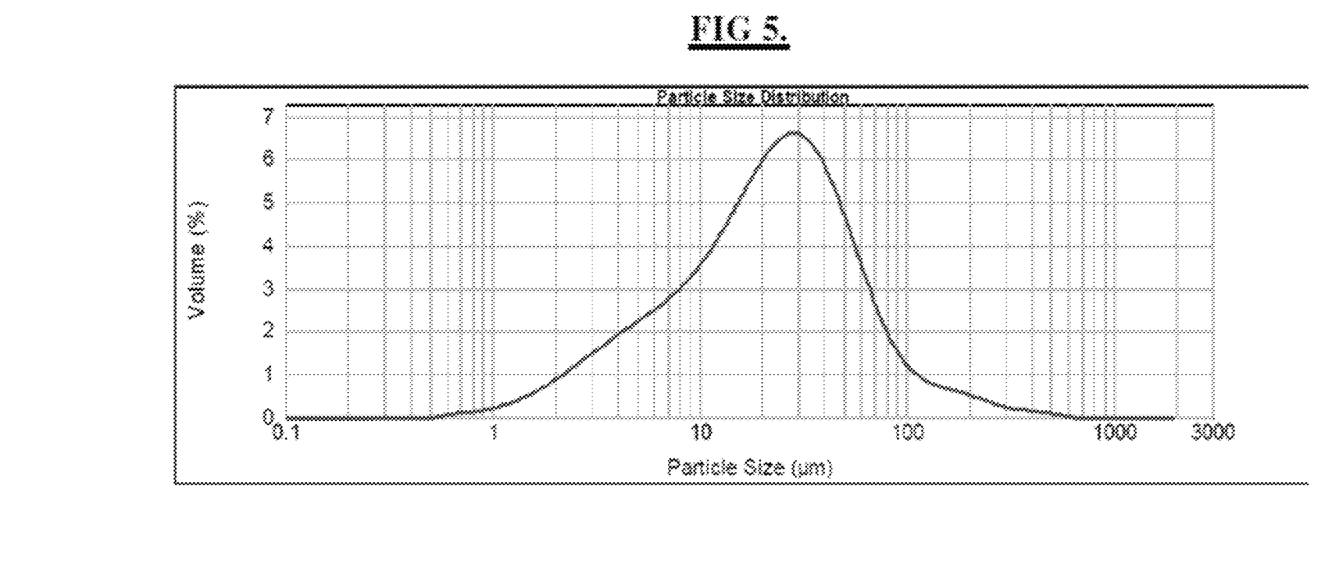
FIG. 5. Particle size distribution of calcium carbonate microcapsules, using sodium caseinate as the shell-forming compound (Example 1).
Figure 6:
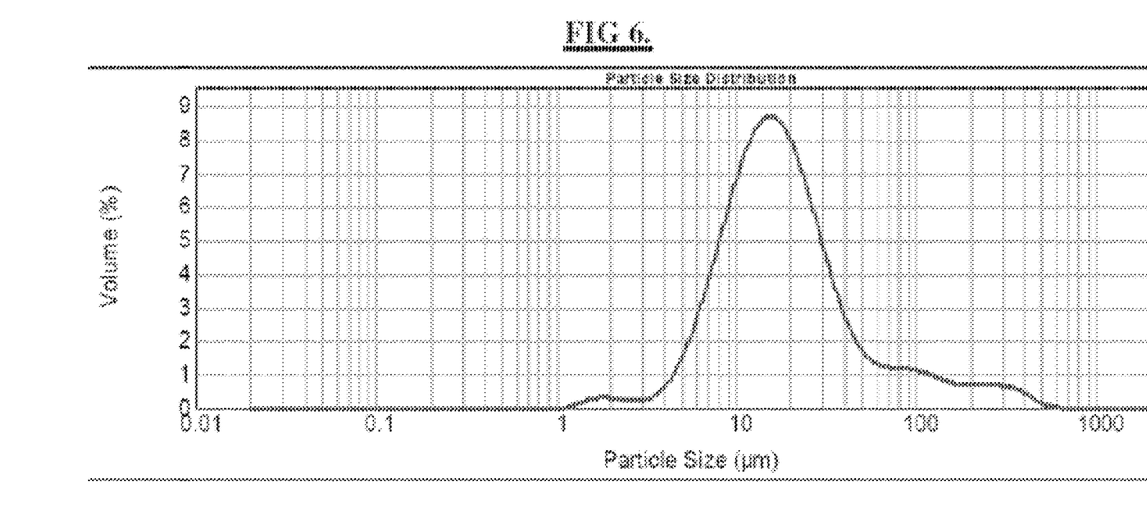
FIG. 6. Particle size distribution of acid-treated calcium carbonate/calcium phosphate microcapsules, using sodium caseinate as the shell-forming compound (Example 2).

The invention relates to a process for the preparation of microcapsules with water-insoluble solids, using charged macromolecules as shell-forming compounds. Shell formation is achieved by ionic gelation induced by the addition of polyvalent cations to the suspension of insoluble solids once the system is at sub-room temperature, which allows a controlled gelation of the charged macromolecules. A subsequent temperature increase consolidates the shell-formation on the insoluble solid particles. The process can be repeated to increase the shell thickness of the microsphere-like microcapsule.

The microcapsules prepared by this process can be single particles or particle agglomerates, depending on the concentration of the charged macromolecules and polyvalent cations. The typical diameter of the capsules prepared by the ionic gelation microencapsulation process is between 0.1 and 1,000 micrometers. The wet system typically produces spherical capsules.

The microcapsules in aqueous suspension can later be dried by spray-drying, where the morphology of the microcapsules can be modified by varying the drying temperature, the pH, the concentration of macromolecules and the concentration of polyvalent cations. For the dry system, it is possible to prepare individual capsules or capsule aggregates with spherical and/or toroidal morphologies. The particle diameter of the agglomerates can vary between 0.2 and 2,000 micrometers.

The shell-forming process using macromolecules and divalent ions allows for the retention of more than 80% of the shell-forming material on the surface of the capsule, which makes the process more efficient. Less than 20% of the shell-forming material remains in solution after the encapsulation process. The water-insoluble solid encapsulation process of the present invention consists of the following steps: a) Elaborating a solution of macromolecules that possess negative charges in their molecular structure.

b) Adjusting the pH of the macromolecule solution and cooling it.

c) Elaborating a suspension of water-insoluble solids, adjusting its pH.

d) Mixing the macromolecule solution from step a) with the suspension of water-insoluble solids, stirring the system and controlling its temperature.

e) Adding a solution of polyvalent ions to the suspension of water-insoluble solids in the presence of negatively-charged macromolecules.

f) Repeating the addition of macromolecule and polyvalent ion solutions to the microencapsulated solid system to increase the thickness of the shell of the microcapsule.

g) Heating the microcapsule suspension.

h) Spray-drying the aqueous microcapsule suspension to obtain dry individual or agglomerated capsules. In an additional embodiment of the invention, the dry microcapsules can again be added to water and acid-treated, in order to use them as a medium for encapsulating water-soluble compounds, such as vitamins, dyes, flavorings, molecules with biocidal activity, fertilizers, drugs, proteins, polysaccharides, among others.

The features of the process for the encapsulation of water-insoluble solids, as well as the features of the capsules obtained by this process are described. These features can be exchanged to describe the process as well as the capsules. Preferably, the water-insoluble solids should have a charged surface when placed in water or another protic solvent, due to the dissociation of its functional groups resulting from interaction with the solvent. Metallic and non-metallic minerals are the preferred insoluble solids for the encapsulation process of the present invention. However, other insoluble solids, such as phyllosilicates, polymeric particles and insoluble solids obtained by synthesis, extraction or bioprocesses, can also be encapsulated using the process described herein.

The formation of charges on the surface of the solid can be monitored by measuring the zeta potential, with absolute values usually above 5 mV. The pH of the system can be adjusted to change the absolute value of the zeta potential, which can promote the adsorption of the charged shell-forming macromolecules. In principle, we seek to produce a pH that maximizes electrostatic attraction between the surface of the solid and the macromolecules without destabilizing the suspension, which can be monitored according to the average particle size.

The proper particle diameter of a water-insoluble solid to be encapsulated by the ionic gelation method of the invention must be greater than 0.1 micrometers and can even reach several millimeters. The suspension's polydispersity is not a hindrance to the microencapsulation process, because the process is homogeneous in the whole system. Neither the morphology, roughness nor porosity of the water-insoluble solid particles are a hindrance to their microencapsulation, because shell formation is uniform across the surface of the solid.

To achieve a homogeneous encapsulation process, the solid concentration in the system must usually remain below 50%, preferably closer to 30% and, depending on the size and geometry of the particle, this value can be decreased to as little as 1%. In the interest of achieving a homogeneous encapsulation process, it is necessary to constantly stir the solid suspension. Usually, stir speeds faster than 500 s$^{-1}$ are enough to prevent particle sedimentation, however, even greater stirring speeds may be needed depending on the size of the suspended particle to be encapsulated. The shell-forming macromolecules are typically negatively charged proteins, polysaccharides or synthetic polymers. The proteins include milk proteins, gelatin, proteins from vegetable sources, albumins and mixtures thereof. Some of these proteins' salts, such as sodium caseinate and calcium caseinate, can also be used. Polysaccharides useful in shell-formation include hydrocolloids such as gum arabic, xanthan gum, alginate salts, cellulose derivatives, pectin salts, carrageenans, guar gum and mixtures thereof.

To achieve adequate hydration and interaction between the macromolecules and the surface of the water-insoluble solids, it is appropriate to decrease the temperature of the system to below-room temperature values, preferably less than 10° C. and temperatures closer to 5° C. are even more preferable.

In order to induce ionic gelation of the macromolecules on the surface of the insoluble solid, a source of polyvalent cations is added to the suspension of solids in the presence of the macromolecules. The source of polyvalent cations should be a water-soluble salt or a slightly water-insoluble salt.

In a preferred embodiment, calcium chloride is employed as the source of polyvalent cations, which can be added directly to the system or, preferably, in a solution with a concentration of up to 2 M. Likewise, the calcium chloride solution can be frozen and added as pieces of ice to the water-insoluble solid suspension. The addition of macromolecules and polyvalent cations at low temperature can be repeated several times to vary the thickness of the shell of the microcapsule, controlling the concentration of each component so as to avoid agglomeration of the suspended particles. Once the adsorption of the macromolecules to the surface of the insoluble solid is carried out, the temperature of the system is increased to induce ionic gelation, which is achieved at temperatures around 25° C. In some cases, the temperature of the system can be increased to 80° C. By increasing the temperature of the suspension in the presence of polyvalent cations, the solid-containing microcapsule is formed. The ionic gelation process leads to high adsorption, greater than 80%, of the macromolecules to the surface of the water-insoluble solid. The microcapsule suspension can then be dried, preferably spray-dried, to obtain dry microcapsules with water-insoluble solids.

Depending on the drying conditions and the macromolecules used as shell-formers, it is possible to produce individual microcapsules or microcapsule agglomerates with shapes ranging from spherical to toroidal agglomerates, which retain their agglomerate identity, despite being redispersed in water.

Due to the agglomerates' stability and inter-particle spaces, these can be used to store compounds inside these spaces. Thus, in an additional embodiment of the invention, a suspension in water of agglomerated microcapsules can be mixed with water-soluble compounds and allow for their diffusion into the inter-particle spaces. These water-soluble compounds can interact with the macromolecules present on the surface of the solid, inducing their adsorption, and are later trapped inside the agglomerated microcapsule due to the formation of a macromolecule film by ionic gelation on the outermost part of the agglomerate.

A preferred embodiment of the invention consists of products that contain a water-soluble compound encapsulated in a microcapsule of water-insoluble solids with a macromolecule shell or encapsulated in an agglomerate of microcapsules of water-insoluble solids. The shell-forming material is preferably at least 10% of the total weight and the preferred macromolecule is sodium caseinate. In an additional embodiment of the invention, the water-insoluble microcapsules obtained by ionic gelation can be used as active ingredients and/or as diluents, excipients or carriers in the preparation of pharmaceutical or nutraceutical compositions.

The compositions that contain the invention's microcapsules can be solid, semi-solid or liquid, and can be prepared using conventional methods widely known in the field, among them are: mixing, granulation, compression, and others, depending on the pursued composition. In a preferred embodiment, the invention's microcapsules are used as an active ingredient and/or as an excipient for direct compression in processes for producing tablets, and can be accompanied by one or more excipients, diluents and pharmaceutically, cosmetically or nutraceutically suitable carriers. The invention is illustrated by the following examples. However, these examples do not limit the scope if the invention.

EXAMPLES

Example 1 Preparation of Calcium Carbonate Microcapsules 54.0 g of a sodium caseinate solution (5% w/w) was prepared by hydration for at least 2 hours, and cooled to 5° C. Its pH was adjusted to 6.5. Separately, 41.2 g of a calcium carbonate suspension (67% w/w) was prepared. Its pH was adjusted to 6.5, it was cooled to 5° C. and it was mixed with the sodium caseinate solution. To achieve a proper mixture of the system, it was stirred at a stir speed of at least 500 $s^{-1}$.

Once the mixture was completed, it was left to stand for 10 minutes at 5° C. to ensure the homogeneity of the system. Then, 4.8 g of a calcium chloride dihydrate solution (4.1% w/w) was slowly added. After this addition, the system was stirred for 5 minutes and its temperature was increased to 25° C. until a suspension of microcapsules was obtained. The suspension was then spray-dried using a Buchi-290 spray-dryer at an entry temperature of 180° C., 32 $m^3$/h of suction, inlet pump speed of 5 mL/min and 1052 L/h air intake.

Example 2. Preparation of Calcium Carbonate-Calcium Phosphate Microcapsules Treated with Acid to Incorporate a Water-Soluble Compound 54.0 g of a sodium caseinate solution (5% w/w) was prepared by hydration for at least 2 hours, and cooled to 5° C. Its pH was adjusted to 6.0. Separately, 41.2 g of a calcium carbonate-calcium phosphate solution (67% w/w) was prepared. Its pH was adjusted to 6.0, it was cooled to 5° C. and it was mixed with the sodium caseinate solution. To achieve a proper mixture of the system, it was stirred at a stir speed of at least 500 $s^{-1}$.

Once the mixture was completed, it was left to stand for 10 minutes at 5° C. to ensure the homogeneity of the system. Then, 4.8 g of a calcium chloride dihydrate solution (4.1% w/w) was added over a period of 2 minutes. After the addition, the system was stirred for 20 minutes and the temperature was increased to 25° C. until a suspension of microcapsules was obtained. This suspension was then dried in a Buchi-290 spray dryer at an entry temperature of 200° C., 32 $m^3$/h of suction, inlet pump speed of 6 mL/min and 1052 L/h air intake.

Then, 40 g of a calcium carbonate-calcium phosphate microcapsule suspension (25%) was prepared and treated with 100 mL of a 1 M solution of ascorbic acid until the decomposition of the calcium carbonate in the microcapsule was deemed complete. Then, the suspension was washed with distilled water to remove the remaining ascorbic acid. The treated microcapsules were retrieved by sedimentation and the wet solid obtained was used to prepare a microcapsule suspension (2%) in the presence of cresyl violet (0.5 ppm). This suspension was cooled to 5° C. for 1.5 hours and then solid sodium caseinate was added to produce a 1% solution.

Afterward, a solution of calcium chloride dihydrate (2 M) was slowly added to achieve a calcium concentration of 20 mM in the final suspension. The system was left to stand for 30 minutes at 5° C. and then at 25° C. to induce the microencapsulation of the cresyl violet. The cresyl violet microcapsule suspension was then washed to remove any non-encapsulated water-soluble dye.

Example 3. Production of Tablets by Direct Compression, Using Calcium Carbonate as an Active Ingredient Calcium carbonate microcapsules (90% $CaCO_3$, 10% sodium caseinate) obtained according to Example 1 were placed in the hopper of a 36-station Rimek® rotary tablet press. The tablet press pressure was set to 25 MPa and a 1390 mg average tablet weight with a processing speed of 500 tablets per minute. The tablets produced by direct compression had an average hardness of 15 kPa and showed good performance in a dissolution test.

REFERENCES

1. Arup Nag, Kyoung-Sik Han, Harjinder Singh. Microencapsulation of probiotic bacteria using pH-induced gelation of sodium caseinate and gellan gum. International Dairy Journal 21 (2011), 247-253.
2. Aude Munin, Florence Edwards-Lévy. Encapsulation of Natural Polyphenolic Compounds; a Review. Pharmaceutics 3 (2011), 793-829.
3. P. Burey, B. R. Bhandari, T. Howes, M. J. Gidley. Hydrocolloid Gel Particles: Formation, Characterization, and Application. Critical Reviews in Food Science and Nutrition, 48 (2008), 361-377.
4. K. Miladia, b, S. Sfar b, H. Fessi a, A. Elaissari. Drug carriers in osteoporosis: Preparation, drug encapsulation and applications. International Journal of Pharmaceutics 445 (2013), 181-195.
5. N. T. Annan, A. D. Borza, L. Truelstrup Hansen. Encapsulation in alginate-coated gelatin microspheres improves survival of the probiotic *Bifidobacterium adolescentis* 15703T during exposure to simulated gastro-intestinal conditions. Food Research International 41 (2008), 184-193.
6. Huiyi Song, Weiting Yua, Meng Gaoa, Xiudong Liub, Xiaojun M. Microencapsulated probiotics using emulsification technique coupled with internal or external gelation process. Carbohydrate Polymers 96 (2013), 181-189.
7. Anil, K. Anal, Willem F. Stevens, Carmen Remuñán-López. Ionotropic cross-linked chitosan microspheres for controlled release of ampicillin. International Journal of Pharmaceutics 312 (2006), 166-173.
8. EP2359929 System for producing microcapsules and use thereof (Universidad de Salamanca (ES); Eva María Martin del Valle (ES); Miguel Angel Galán Serrano (ES); Edgar Pérez Herrero (ES) Aug. 28 2011).
9. Flavia N. Souza, Clarice Gebara, María C E. Ribeiro, Karina S. Chaves, Mirna L. Gigante, Carlos R. F. Grosso. Production and characterization of microparticles containing pectin and whey proteins. Food Research International 49 (2012), 560-566.
10. Qiu-Yue Dong, I Meng-Yan Chen, I Yang Xin, I Xue-Yan Qin, I Zhuo Cheng, I Lu-E Shil* & Zhen-Xing Tang. Alginate-based and protein-based materials for probiotics encapsulation: a review. doi: 10.1111/ijfs.12078.
11. US 2007/0275080 Polymer-based microstructures (Engineered Release Systems Inc. (US); Bryan E. Laulicht (US); Sasha Bakhru (US) Nov. 29, 2007.
12. WO 1992/05708 Improved microencapsulation process and products (Griffith Laboratories Worldwide Inc.; Joseph Janda (US); Donald Bernacchi (US); Suzanne Frieders (US) Apr. 16, 1992).

The invention claimed is:
1. A process for encapsulating one or more water-insoluble solids in microcapsules by means of ionic gelation, comprising the following steps:
 a) providing a solution of negatively charged macromolecules selected from the group consisting of proteins, polysaccharides and mixtures thereof;
 b) providing an aqueous suspension of the water-insoluble solids independently selected from the group consisting of metallic and non-metallic minerals, phyllosilicates, polymeric particles and insoluble solids obtained via synthesis, extraction or bioprocesses;
 c) mixing the solution of negatively charged macromolecules from step a) and the aqueous suspension from step b) under stirring and lowering the temperature to sub-room temperature values between 5° C. and 20° C.;
 d) adding a source of polyvalent cations to the aqueous suspension of step c);
 e) increasing the temperature of the system between room temperature and 80° C.

2. The process according to claim 1, wherein the pH of the solution from step a) is adjusted to achieve an absolute zeta potential above 5 mV.
3. The process according to claim 1, wherein steps c) and d) are repeated one or more times to increase the thickness of the shell that covers the insoluble solid.
4. The process according to claim 1, wherein the microcapsules are subjected to an additional drying step with a spray dryer at temperatures equal to or greater than 180° C.
5. The process according to claim 1, wherein the one or more insoluble solids are selected from the group consisting of insoluble calcium salts, kaolin, silica, and metallic oxides.
6. The process according to claim 1, wherein the concentration of insoluble solids in the aqueous suspension of step b) is between 5% and 70% (w/w).
7. The process according to claim 1, wherein the negatively charged macromolecule is sodium caseinate.
8. The microcapsules obtained according to the process of claim 1, comprising one water-insoluble solid encapsulated in a macromolecules shell, wherein:
 the water-insoluble solid is selected from the group consisting of metallic and non-metallic minerals, phyllosilicates, polymeric particles and insoluble solids obtained via synthesis, extraction or bioprocesses;
 the macromolecules are selected from the group consisting of proteins, polysaccharides and mixtures thereof;
 said macromolecules constitutes at least 10% of the total weight of the microcapsule; and
 at least 80% of the macromolecules are adsorbed on the surface of the water-insoluble solid.
9. The process according to claim 1, wherein the source of polyvalent cations is water-soluble calcium chloride.
10. The microcapsules according to claim 8, wherein the water-insoluble solid is selected from the group consisting of calcium carbonate, calcium phosphate, silica, titanium dioxide and kaolin.
11. A composition comprising the microcapsules according to claim 8, wherein the encapsulated insoluble solid is in the form of agglomerates.
12. A composition comprising the microcapsules according to claim 8 as a diluent, excipient or carrier.
13. A composition comprising the microcapsules according to claim 8 as an active ingredient and/or excipient for direct compression.
14. A composition comprising the microcapsules according to claim 8 as an active ingredient.
15. The composition according to claim 14 further comprising a pharmaceutically, cosmetically, or nutraceutically suitable carrier.
16. A process for encapsulating a water-soluble compound in microcapsules comprising one or more water-insoluble solids, comprising the following steps:
 a) providing an aqueous suspension of microcapsules comprising two insoluble solids (A) and (B), wherein (A) is stable and (B) is susceptible to degradation or dissolution in the presence of a degrading or dissolving agent, independently selected from the group consisting of metallic and non-metallic minerals, phyllosilicates, polymeric particles and insoluble solids obtained via synthesis, extraction or bioprocesses;
 wherein said microcapsules are prepared as in claim 1;
 b) adding a degrading or dissolving agent to the suspension of step a) until the degradation or dissolution of insoluble solid (B) is achieved;
 c) removing the excess of degrading or dissolving agent from the suspension of step b);

d) adding a water-soluble compound to the aqueous suspension of step c);

e) providing a solution of negatively charged macromolecules selected from the group consisting of proteins, polysaccharides and mixtures thereof;

f) mixing the solution of macromolecules of step e) and the suspension of step d) under stirring and lowering the temperature to sub-room temperature values between 5° C. and 20° C.;

g) adding a source of polyvalent cations to the aqueous suspension of step f);

h) increasing the temperature of the system between room temperature and 80° C.

17. The process according to claim 16, wherein the insoluble solid (A) is selected from the group consisting of calcium phosphate, kaolin, silica, metallic oxides, and mixtures thereof.

18. The process according to claim 16, wherein the insoluble solid (A) is calcium phosphate.

19. The process according to claim 16, wherein the insoluble solid (B) is selected from the group consisting of calcium carbonate, metallic oxides, and mixtures thereof.

20. The process according to claim 16, wherein the insoluble solid (B) is calcium carbonate.

21. The process according to claim 16, wherein the degrading or dissolving agent is selected from a pH modification agent, a complexing processes agent, a photodegradation agent and a hydrolysis agent.

22. The process according to claim 16, wherein the degrading or dissolving agent is a pH modification agent.

23. The process according to claim 16, wherein the water-soluble compound from step d) is selected from the group consisting of vitamins, colorings, flavorings, scents, biocides, fertilizers, drugs, proteins, polysaccharides and mixtures thereof.

24. The process according to claim 16, wherein steps f) and g) are repeated one or more times to increase the thickness of the shell that covers the microcapsule.

25. The process according to claim 16, wherein the microcapsules can be subjected to an additional drying step with a spray dryer at temperatures equal to or greater than 180° C.

26. The process according to claim 16, wherein an additional drying step is carried out to dehydrate the microcapsule.

27. The process according to claim 16, wherein the concentration of microcapsules containing insoluble solids in the aqueous suspension of step a) is between 1.0% and 70.0% (w/w).

28. The process according to claim 16, wherein the negatively charged macromolecule is sodium caseinate.

29. A product obtained according to the process of claim 16, comprising a water-soluble compound encapsulated in a microcapsule of water-insoluble solids with a macromolecule shell, wherein:

the macromolecule is selected from the group consisting of proteins, polysaccharides and mixtures thereof;

the water-insoluble solid is selected from the group consisting of metallic and non-metallic minerals, phyllosilicates, polymeric particles and insoluble solids obtained via synthesis, extraction or bioprocesses;

the water-soluble compound is selected from the group consisting of vitamins, colorings, flavorings, scents, biocides, fertilizers, drugs, proteins, polysaccharides and mixtures thereof;

at least 80% of the macromolecules are adsorbed on the water-insoluble solid surface; and the water soluble compound is diffused into the water-insoluble solid.

30. The product according to claim 29, wherein the macromolecules constitutes at least 10% of the total weight.

31. The product according to claim 29, wherein the macromolecule is sodium caseinate.

32. The product according to claim 29, wherein the water-insoluble solid is selected from the group consisting of calcium carbonate, calcium phosphate, silica, titanium dioxide and kaolin.

33. A composition comprising a product according to claim 29, wherein the microcapsules encapsulating the water-soluble solid are in the form of agglomerates.

34. A water-soluble compound encapsulated in a microcapsule of water-insoluble solids with a macromolecule shell, wherein:

the macromolecule is selected from the group consisting of proteins, polysaccharides and mixtures thereof; and the water-insoluble solid is selected from the group consisting of metallic and non-metallic minerals, phyllosilicates, polymeric particles and insoluble solids obtained via synthesis, extraction or bioprocesses;

at least 80% of the macromolecules are adsorbed on the water-insoluble solid surface; and the water soluble compound is diffused into the water-insoluble solid.

* * * * *